(12) United States Patent
Sarvestani (10) Patent No.: US 10,030,992 B2
(45) Date of Patent: Jul. 24, 2018

(54) BICYCLE ACTIVITY MONITORING AND RECORDING DEVICE

(71) Applicant: Seyed Amin Ghorashi Sarvestani, Keppel Bay (SG)

(72) Inventor: Seyed Amin Ghorashi Sarvestani, Keppel Bay (SG)

( * ) Notice: Subject to any disclaimer, the term of this patent is extended or adjusted under 35 U.S.C. 154(b) by 1143 days.

(21) Appl. No.: 14/247,346

(22) Filed: Apr. 8, 2014

(65) Prior Publication Data

US 2015/0285657 A1 Oct. 8, 2015

(51) Int. Cl.
| | | |
|---|---|---|
| *G01C 22/00* | (2006.01) | |
| *A61B 5/0245* | (2006.01) | |
| *A61B 5/00* | (2006.01) | |
| *A61B 5/11* | (2006.01) | |
| *G01K 13/00* | (2006.01) | |
| *G01C 5/00* | (2006.01) | |
| *G01S 19/19* | (2010.01) | |

(52) U.S. Cl.
CPC .......... *G01C 22/002* (2013.01); *A61B 5/0245* (2013.01); *A61B 5/1118* (2013.01); *A61B 5/6895* (2013.01); *G01C 5/00* (2013.01); *G01K 13/00* (2013.01); *G01S 19/19* (2013.01)

(58) Field of Classification Search
CPC .......... B62J 6/001; G01C 22/002; G01C 5/00; A61B 5/0245; A61B 5/6895; A61B 5/1118; G01K 13/00; G01S 19/19
USPC .......................................... 280/281; 264/129
See application file for complete search history.

(56) References Cited

U.S. PATENT DOCUMENTS

| | | | | |
|---|---|---|---|---|
| 4,319,581 A | * | 3/1982 | Cutter ................... | A61B 5/024 600/382 |
| 6,165,129 A | * | 12/2000 | Bates ..................... | A61B 5/222 600/382 |
| 2005/0195094 A1 | * | 9/2005 | White ................ | A63B 24/0021 340/870.01 |
| 2009/0063049 A1 | * | 3/2009 | Swisher ............. | A63B 24/0062 701/469 |
| 2009/0278734 A1 | * | 11/2009 | Haataja .............. | A63B 24/0062 342/357.57 |
| 2010/0198453 A1 | * | 8/2010 | Dorogusker ....... | A63B 24/0062 701/31.4 |
| 2012/0310442 A1 | * | 12/2012 | Doutaz .................. | G01C 21/12 701/1 |
| 2012/0323485 A1 | * | 12/2012 | Mutoh ............... | G01C 21/3617 701/428 |
| 2013/0205896 A1 | * | 8/2013 | Baechler .................. | B62J 99/00 73/493 |
| 2014/0002060 A1 | * | 1/2014 | Mizutani ................ | G01P 3/481 324/163 |

* cited by examiner

*Primary Examiner* — Sundhara Ganesan
(74) *Attorney, Agent, or Firm* — Emerson Thomson Bennett LLC (57) ABSTRACT

An activity monitoring and recording device may include a smartphone, a magnet, a hall-effect sensor, a Global Positioning System (GPS) device, a microprocessor and proprietary software supported to a bicycle. The software may determine bicycle and rider information including speeds, distance traveled, average speed, and calories burned by the rider during a ride.

5 Claims, 5 Drawing Sheets

BICYCLE ACTIVITY MONITORING AND RECORDING DEVICE

I. BACKGROUND

A. Field of the Invention

This invention generally relates to bicycles and more specifically to methods and apparatuses related to bicycle activity monitoring and recording.

B. Description of Related Art

Bicycles and other manually propelled vehicles are well known. It is known to provide bicycles with speedometers that indicate the speed of the bicycle. It is also known to manually monitor and record activities related to a bicycle ride, such as distance traveled and time spent during the ride.

What is needed is a device that can automatically monitor and record activities related to bicycling.

II. SUMMARY

According to one aspect of this invention, an activity monitoring and recording device may be used with a manually propelled bicycle that includes: a body; first and second wheels that (1) are rotatably supported to the body so that the wheels are rotatable with respect to the body; (2) have ground engaging surfaces that engage a ground surface as the bicycle is propelled over the ground surface and the wheels are thereby rotated with respect to the body; and, a handle bar that is supported to the body. The activity monitoring and recording device may comprise: a first magnet that: (1) is supportable to the first wheel; and, (2) is rotatable with the first wheel when the first wheel is rotated with respect to the body; a conductive surface that (1) is supportable to the handle bar; (2) determines heartbeat data of a rider when a hand of the rider contacts the conductive surface while the rider manually propels the bicycle during a first ride; and, (3) transmits the heartbeat data; a smartphone that: (1) comprises a smartphone microprocessor; (2) comprises a Global Positioning System (GPS) device: and, (3) comprises a display screen; a base that: (1) comprises a base unit microprocessor; (2) comprises a hall effect sensor; and (3) comprises software that can determine speeds of the bicycle during the first ride based on data from the hall effect sensor and the first magnet; a first cradle that supports the smart phone to the handle bar; a second cradle that supports the base unit to the body juxtaposed to the first magnet at least once per revolution of the first wheel; wherein the smartphone communicates with the base unit; wherein at least one of the smartphone microprocessor and the base unit microprocessor: (1) can determine a distance traveled by the bicycle during the first ride based on data from the GPS device; (2) can determine an average speed of the first ride; (3) is accessible to receive imputed information regarding a profile of the rider and information regarding a profile of the bicycle; (4) can determine calories burned by the rider during the first ride based on the heartbeat data, the rider's profile, the bicycle's profile, the distance traveled daring the first ride, and the average speed of the first ride; and, (5) comprises computer memory that can store: (a) the speeds of the bicycle during the first ride; (b) the distance traveled during the first ride; (c) the average speed of the first ride; (d) the imputed information regarding the rider's profile; (e) the imputed information regarding the bicycle's profile; (f) the heartbeat data transmitted to the base unit; and, (g) the calories burned by the rider during the first ride; and, wherein the smartphone display screen displays to the rider during the first ride; the imputed information regarding the profile of the rider; the information regarding the profile of the bicycle; data provided by the GPS device; and at least one of: (1) the speeds of the bicycle during the first ride; (2) the distance traveled by the bicycle during the first ride; (3) the average speed of the first ride; and, (4) the calories burned by the rider during the first ride.

According to another aspect of this invention, the activity monitoring and recording device may comprise: a thermal sensor; and, an altitude sensor. At least one of the smartphone microprocessor and the base unit microprocessor: (1) can determine atmospheric temperatures during the first ride; (2) can determine altitudes of the bicycle during the first ride; and, (3) can determine calories burned by the rider during the first ride based on the atmospheric temperatures and the altitudes. The computer memory can store: (1) the atmospheric temperatures, and, (2) the altitudes; and, the smartphone display screen displays to the rider during the first ride; (1) the atmospheric temperatures; and, (2) the altitudes.

According to another aspect of this invention, the smartphone display screen displays to the rider during the first ride: the speeds of the bicycle during the first ride; the distance traveled by the bicycle during the first ride; the average speed of the first ride; and, the calories burned by the rider during the first ride.

According to another aspect of this invention, the conductive surface determines heartbeat data of the rider when the hand of the rider contacts the conductive surface while the rider manually propels the bicycle during a second ride: at least one of the smartphone microprocessor and the base and microprocessor (1) can determine a distance traveled by the bicycle during the second ride based on data from the GPS device; (2) can determine an average speed of the second ride; (3) can determine calories burned by the rider during the second ride based on the heartbeat data, the rider's profile, the bicycle's profile, the distance traveled during the second ride, and the average speed of the second ride; (4) can determine atmospheric temperatures during the second ride; (5) can determine altitudes of the bicycle during the second ride; and (6) computer memory can store: (a) the speeds of the bicycle during the second ride; (b) the distance traveled during the second ride; (c) the average speed of the second ride; (d) the atmospheric temperatures during the second ride; (e) the altitudes during the second ride; and, (d) the calories burned by the rider during the second ride; and, the smartphone display screen displays to the rider during the second ride; (1) the imputed information regarding the profile of the rider; (2) the information regarding the profile of the bicycle; (3) data provided by the GPS device during the second ride; (4) the speeds of the bicycle during the second ride; (5) the distance traveled by the bicycle during the second ride; (6) the average speed of the second ride; (7) the atmospheric temperatures during the second ride; (8) the altitudes during the second ride; and, (9) the calories burned by the rider during the second ride.

According to another aspect of this invention, the conductive surface is part of an elastic grip that is attachable to the handle bar of the bicycle and to the second bicycle; and, a battery powered transmitter is positioned within the elastic grip and transmits the heartbeat data to at least one of the smartphone and the base unit.

According to another aspect of this invention, the smartphone and the base unit composes between them: (1) a Bluetooth communication port; and, (2) a Universal Serial Bus (USB) interface.

According to another aspect of this invention, the smartphone and the base unit can communicate via at least one of: a modem and Wi-Fi.

According to another aspect of this invention, the smartphone can transfer data related to at least one of the first ride and the second ride to at least one of a tablet computer, a lap top computer, another smartphone and, a desk top computer.

According to another aspect of this invention, the smartphone can transfer the data related to at least one of the first ride and the second ride via a wired connection and wirelessly.

One advantage of this invention, according to some embodiments of this invention, is that numerous bicycle activities can be automatically monitored and recorded.

Another advantage of this invention, according to some embodiments of this invention, is that bicycle activity information can be stored for numerous riders and numerous bikes.

Still another advantage of this invention, according to some embodiments of this invention, is that the inventive device can be accessed using an electronic device to provide inputted information regarding rider profile(s) and/or vehicle profile(s).

Other benefits and advantages of this invention will become apparent to those skilled in the art to which it pertains upon reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

IV. DETAILED DESCRIPTION

Figure 1:
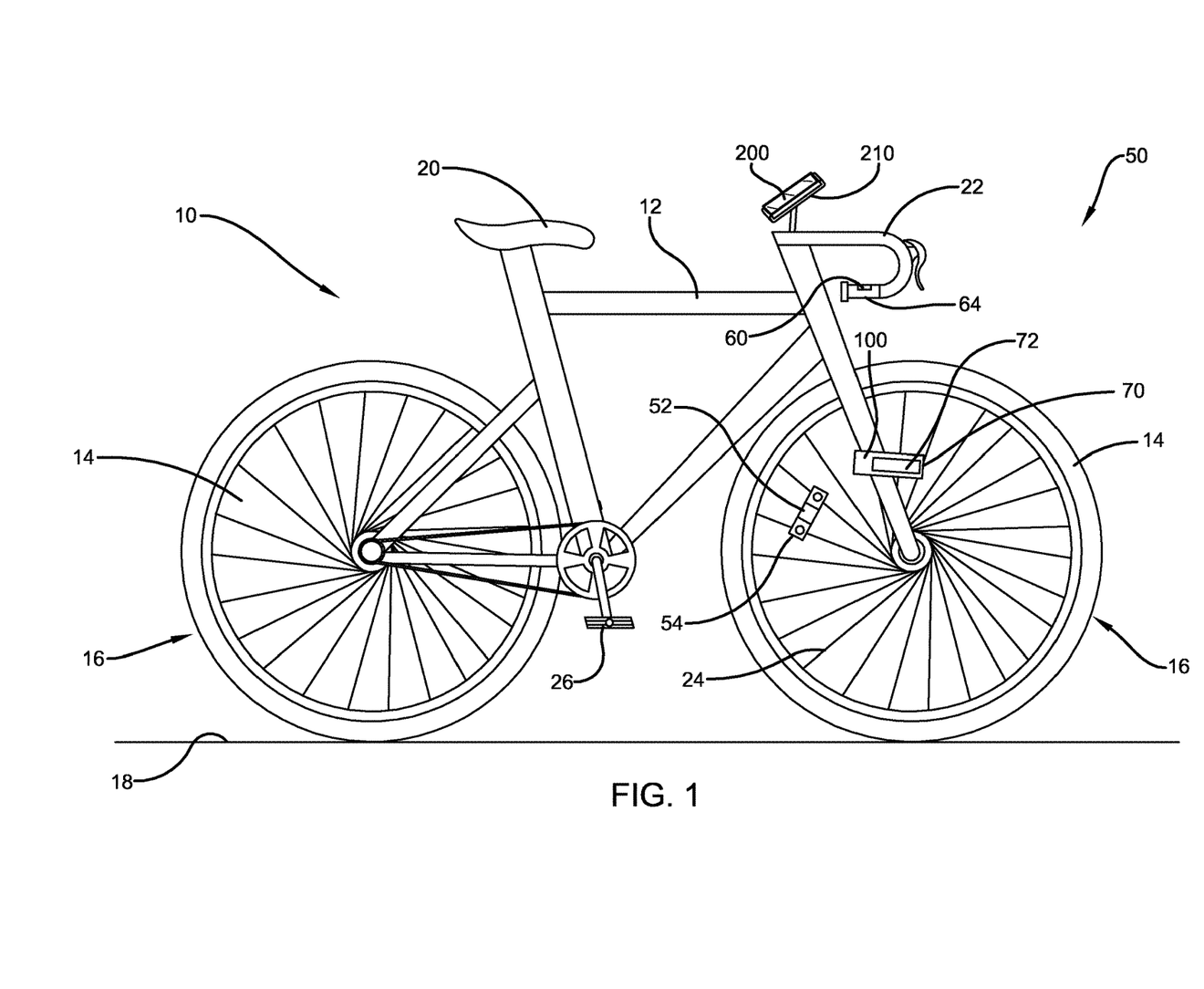
FIG. 1 is a side view of a bicycle that has an activity monitoring and recording device according so some embodiments of this invention.

Referring now to the drawings wherein the showings are for purposes of illustrating embodiments of the invention only and not for purposes of limiting the same, and wherein like reference numerals are understood to refer to like components. FIG. 1 shows a manually propelled vehicle 10 which might be used with a smartphone 200 and an activity monitoring and recording device 50 according to some embodiments of this invention. By manually propelled vehicle it is meant any vehicle that can be propelled or driven by a man or woman's own physical power. One non-limiting example of manually propelling is via bicycle pedals 26 that are rotated by the rider's feet and legs as is well known to those of skill in the art. While the manually propelled vehicle shown is a bicycle, it should be understood that any manually propelled vehicle chosen with the sound judgment of a person of skill in the art can be used with this invention. Non-limiting examples of manually propelled vehicles include, unicycles, bicycles, tricycles, wagons, and go-carts. The manually propelled vehicle 10 may include a body or frame 12 and at least one wheel 14, two shown, that is rotatably supported to the body 12 so that the wheel 14 is rotatable with respect to the body 12. Each wheel 14 may have a ground engaging surface 16 that engages a ground surface 18 as the vehicle 10 is propelled over the ground surface 18 and the wheel 14 is thereby rotated with respect to the body 12. The vehicle 10 may also haven seat 20 supported to the body 12 upon which a rider may be supported in a known manner. The vehicle 10 may also have a hand engaging surface 22 supported to the body 12 that the rider's hand(s) may contact. For the embodiment shown, the hand engaging surface 22 is a handle bar though any hand engaging surface chosen with the sound judgment of a person of skill in the art may be used with this invention.

Figure 2:
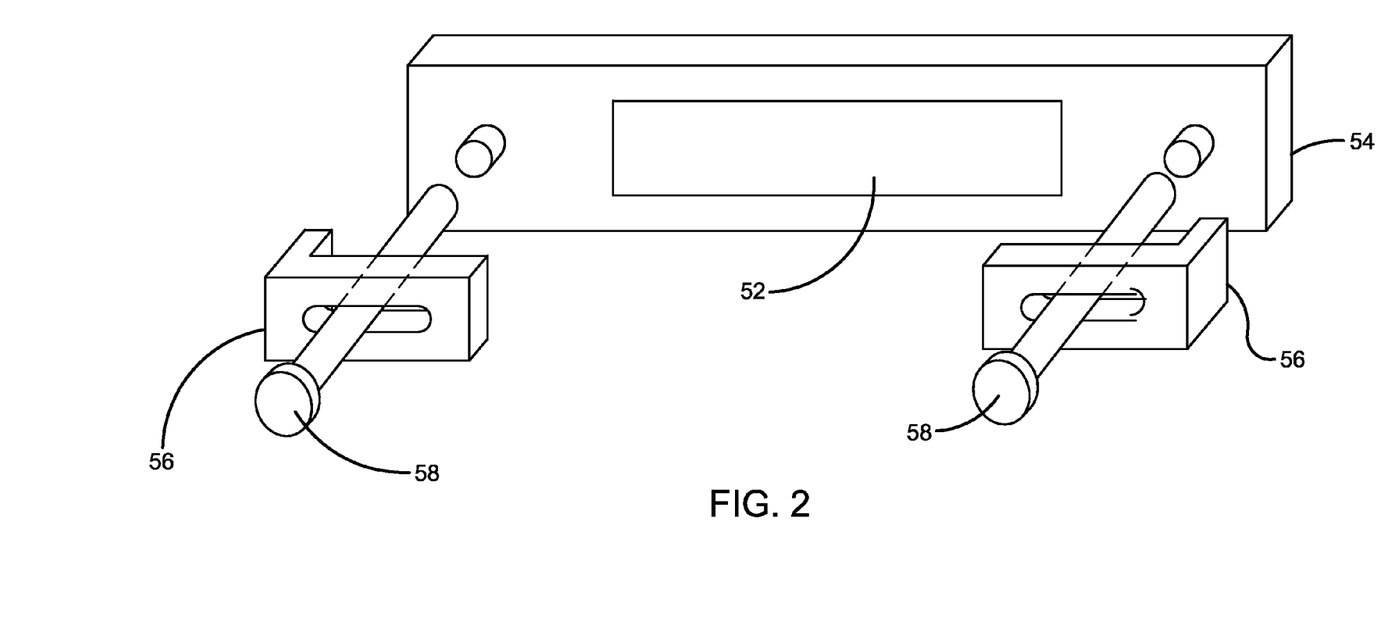
FIG. 2 is a perspective view of a magnet and magnet housing.

With reference now to FIGS. 1 and 2, the activity monitoring and recording device 50 may include a magnet 52 thin is supportable to one of the wheels 14 and is rotatable with the wheel 14 when the wheel 14 is rotated with respect to the body 12. While the magnet 52 may be supported to the wheel 14 in any manner chosen with the sound judgment of a person of skill in the art, for the embodiment shown, the magnet 52 is positioned within a magnet housing 54. The housing 54 and magnet 52 are then supported to one or more wheel spokes 24 using one or more magnet brackets 56 and one or more connectors 58. The one or more connectors 58 may pass through openings in the one or more magnet brackets 56, between the spokes 24, and be received in one or more openings formed in the magnet housing 54, as shown.

Figure 3:
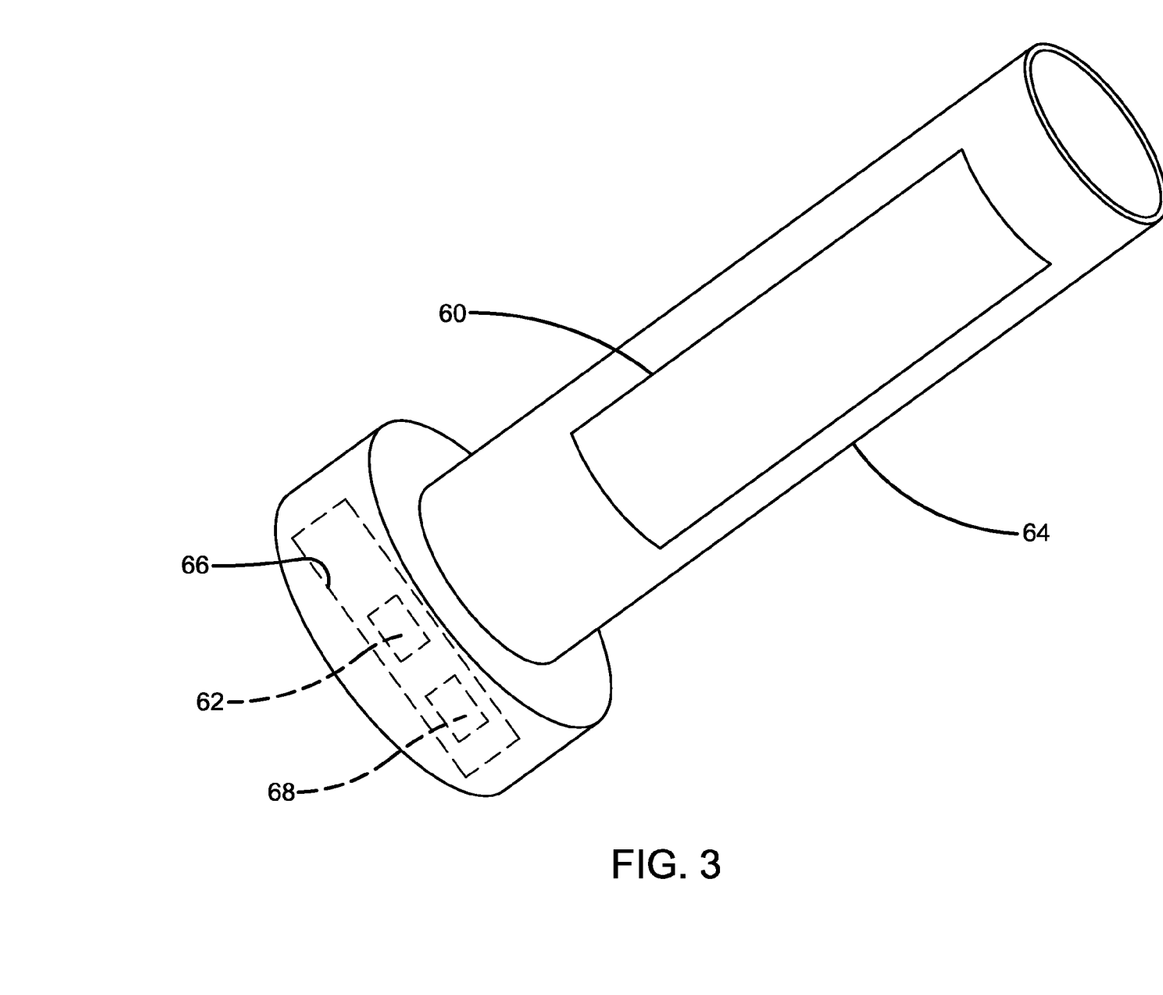
FIG. 3 is a perspective view of a conductive surface with an elastic grip.

With reference now to FIGS. 1 and 3, the activity monitoring and recording device 50 may include a conductive surface 60 that is supportable to the hand engaging surface 22 and that determines heartbeat data of the rider when a hand of the rider contacts the conductive surface 60 while the rider manually propels the vehicle during is ride. A transmitter 62 may be used to transmit the heartbeat data. In one embodiment, the transmitter 62 transmits wirelessly. The conductive surface 60 may be supported to the hand engaging surface 22 in any manner chosen with the sound judgment of a person of skill in the art. For the embodiment shown, the conductive surface 60 is placed within an elastic grip 64 that has an opening that receives a portion of the hand engaging surface 22. The grip 64 may include a compartment 66 into which the transmitter 62 and a battery 68 may be positioned. The battery 68 may be used to power the conductive surface 60 and to power the transmitter 62 in is known manner. In one embodiment, the battery 68 may be rechargeable. The conductive surface 60 may sense the rider's heartbeat data when, for example, the rider's palm is placed onto the conductive surface 60.

Figure 4:
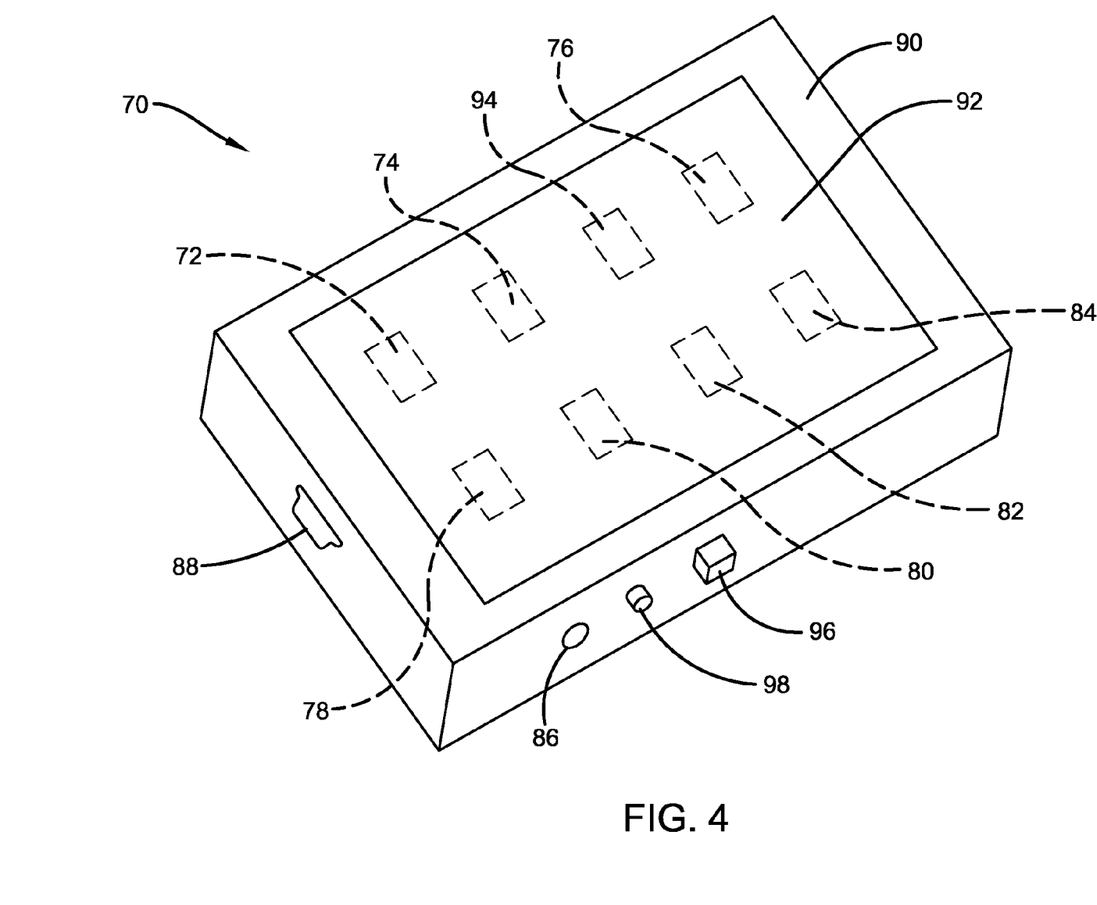
FIG. 4 is a perspective view of a base unit.

With reference now to FIGS. 1 and 4, the activity monitoring and recording device 50 may include a smartphone 200 and a base unit 70 that has a microprocessor 72, proprietary software 74 (which may also be provided on the smartphone 200) and a hall-effect sensor 76. The rose unit 70 may be position so that the hall-effect sensor 76 is juxtaposed to the magnet 52 at least once per revolution of the wheel 14, as shown in FIG. 1. In this way the hall-effect sensor 74, magnet 52 and proprietary software 74 can be used to determine the speeds of the vehicle 10 during as ride based on the relevant magnetic fields. The proprietary software 74 may also be capable to determine the average speed of the vehicle 10 during a ride. The smartphone 200 and/or base unit 70 may have computer memory 78 that can store data of many types, including the riders heartbeat data, the speeds of the vehicle 10 and the average speed of the vehicle 10. The smartphone 200 and/or base unit 70 may include a Global Positioned System (GPS) device 80 that works with a GPS to determine the location of the vehicle 10. The software 74 may use data from the GPS device 80 to determine the distance traveled by the vehicle during a ride and the memory may 78 may store the location data and/or the distance traveled data.

With continuing reference to FIGS. 1 and 4, the smartphone 200 and/or base unit 70 may include or work with any sensor chosen with sound judgment of a person of skill in the art to monitor the vehicle 10 and/or the rider of the vehicle. In one embodiment, a thermal sensor 82 that senses the atmospheric temperature at the location of the vehicle 10 is used. In another embodiment, an altitude sensor 84 that senses the altitude of the vehicle 10 as it travels is used. The software 74 on the smartphone 200 and/or base unit may include memory 78 used to track and record the atmospheric temperatures and altitudes throughout a ride. This data may be used by the software 74 to determine/calculate any useful data as determined by a person of skill in the art, including calories burned by the rider during a ride.

Still referring to FIGS. 1 and 4, the proprietary software 74 on the smartphone 200 or base unit may be accessible by an electronic device to provide inputted information regarding a profile of one or more riders and inputted information regarding a profile of one or more vehicles. Non-limiting examples of rider profile information includes rider age, rider weight, rider sex, average heartbeat rate, ride begin times and end times, and ride dates. Non-limiting examples of vehicle profile information includes vehicle type, vehicle wheel size, and vehicle weight. Once inputted into the base unit 70, the profile information can be used by the software 74, along with the heartbeat data, to determine the calories burned by the rider during the ride. The memory 78 can store the profile data and thus the same profile data will not have to be inputted again but the software 74 can use the profile data for future determinations/calculations. The profile information may be inputted into the software 74 in any manner chosen with the sound judgment of a person of skill in the art. In one embodiment, the data is inputted wirelessly in a known manner. In another embodiment, the base unit 70 has a Bluetooth communication port 86. In yet another embodiment, the base unit 70 has a Universal Serial Bus (USB) interface 88. The wireless, Bluetooth and USB communication devices can be used to send and receive any data chosen with the sound judgment of a person of skill in the art. The software 74 may be accessed to input data from a rider in any applicable manner, including but not limited to smartphones, tablet computers, lap top computers and desk top computers.

With continuing reference to FIGS. 1 and 4, the smartphone 200 may include a display screen which may be a touch screen. The base unit may include a housing 90 and a display screen 92 which may be a touch screen. In one embodiment, the display screen(s) may be used by the rider may for access. The smartphone 200 and/or base unit 70 may also have any operating components as chosen by a person of skill in the art. In one embodiment, the base unit 70 includes solar cells 94 so that the base unit 70 can be powered by solar energy. A power on/off switch 96 may be provided so that the rider can easily turn the base unit 70 on and off. An LED indicator 98 may be provided to indicate the power status (on or off).

Figure 5:
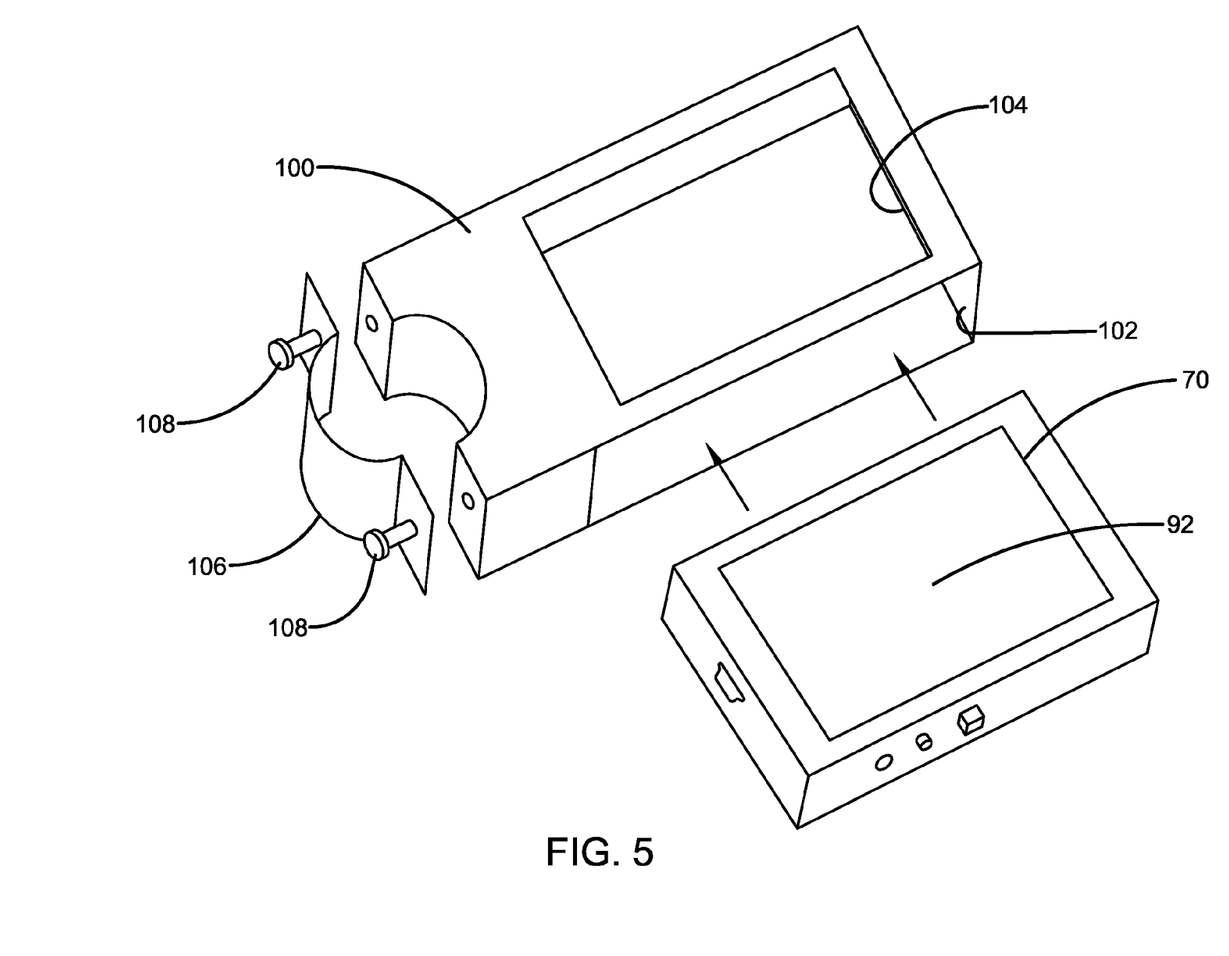
FIG. 5 is a perspective view of a base unit and cradle.

With reference now to FIGS. 1 and 5, to support the base unit 70 to the vehicle 10, a cradle 100 may be used. The cradle 100 may include a cavity 102 into which the base unit 70 may be inserted the protection during use. The cradle 100 may have an opening 104 through which the display screen 92 can be viewed when the base unit 70 is received within the cradle 100. The cradle 100 and base unit 70 may then be supported to the vehicle body using one or more cradle brackets 106 and one or more connectors 108. The one or more connectors 108 may pass through openings in the one or more cradle brackets 56, around a portion of the body 12, such as the wheel fork, as shown, and be received in one or more openings formed in the cradle 100. Another cradle 210 may be used to support the smartphone 200 to the vehicle 10, such as to the handle bars.

With reference now to all the FIGURES, to use the activity monitoring and recording device 50 of this invention, the rider may attach a magnet 52 to a wheel 14 in a manner described above. If used, the rider may also attach the conductive surface 60 to the hand engaging surface 22 in a manner described above. The rider may input any desired profile information into the smartphone 200 and/or base unit 70 concerning the rider and/or the vehicle, as described above, and insert the base unit 70 within the cradle 100 and the smartphone 200 within its cradle 210. The rider may then attach the cradles, smarts 200 and base unit 70 to the vehicle. Once the components are supported to the vehicle 10, the rider need only ride the vehicle. During the ride, the rider may access the smartphone 200 continually or as desired to monitor any desired information, such as burned calories. Once the ride is complete, the rider may access the base unit 70 to review any desired information it contains.

With continuing reference to all the FIGURES, it should be understood that this invention is useful for numerous vehicle, rides, and riders. A first rider, for example, may input his/her rider profile information into the smartphone 200 and/or base unit 70 just once and the memory 78 will store it. Similarly, the vehicle profile information for a first vehicle may be inputted into the smartphone 200 and/or base unit 70 just once. As a result, should the same first rider use the same first vehicle for a second ride, the rider and vehicle profile information will not have to be re-inputted (only changes to the original profile information will have to be inputted). This is very easy for the rider. The software 74 may then be able to calculate/determine comparative data between the first and second rides for the first rider—such as the calories burned during the rides. Should the same first rider then choose to ride a second vehicle, it is only necessary for the second vehicle to be equipped with the same magnet and conductive surface (or, if desired, another magnet and conductive surface). The first rider then only needs to input the profile information for the second vehicle into the same smartphone 200 or base unit and attach the same smartphone 200 and/or base unit to the second vehicle. At the conclusion of the third lade, the software may then be able to calculate/determine comparative data between the first, second and third rides for the first rider. Similarly, a second rider may use the same base unit with the same or other vehicles and will only need to input new profile information regarding the rider and/or vehicle. Once again, the software may then be able to calculate/determine comparative data between rides and riders. In another embodiment, fleets of riders and/or vehicles can be monitored. If desired, additional base units may also be used. In this case, different base units may be connected together in a known manner to permit data to be shared.

Numerous embodiments have been described herein. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof. Further, the "invention" as that term is used in this document is what is claimed in the claims of this document. The right to claim elements and/or sub-combinations that are disclosed herein as other inventions in other patent documents is hereby unconditionally reserved.

What is claimed is:

1. An activity monitoring and recording device for use with a manually propelled bicycle comprising: a body; first and second wheels that: (1) are rotatably supported to said body so that said wheels are rotatable with respect to said body; (2) have ground engaging surfaces that engage a ground surface as said bicycle is propelled over said ground surface and said wheels are thereby rotated with respect to said body; and, a handle bar that is supported to said body; said activity monitoring and recording device comprising: a first magnet that: (1) is supportable to said first wheel; and, (2) is rotatable with said first wheel when said first wheel is rotated with respect to said body; a conductive surface that: (1) is supportable to said handle bar; (2) determines heartbeat data of a rider when a hand of said rider contacts said conductive surface while said rider manually propels said bicycle during a first ride; and, (3) transmits said heartbeat data; a smartphone that: (1) comprises a smartphone microprocessor; (2) comprises a Global Positioning System GPS device; and, (3) comprises a display screen; a base unit that: (1) comprises a base unit microprocessor; (2) comprises a hall effect sensor; and, (3) comprises software that can determine speeds of said bicycle during said first ride based on data from said hall effect sensor and said first magnet; a first cradle that supports said smart phone to said handle bar; a second cradle that supports said base unit to said body juxtaposed to said first magnet at least once per revolution of said first wheel; wherein said smartphone communicates with said base unit wherein at least one of said smartphone microprocessor and said base unit microprocessor: (1) can determine a distance traveled by said bicycle during said first ride based on data from said GPS device; (2) can determine an average speed of said first ride; (3) is accessible to receive imputed information regarding a profile of said rider and information regarding a profile of said bicycle; (4) can determine calories burned by said rider during said first ride based on said heartbeat data said rider's profile, said bicycle's profile, said distance traveled during said first ride, and said average speed of said first ride; and, (5) comprises computer memory that can store: (a) said speeds of said bicycle during said first ride; (b) said distance traveled during said first ride; (c) said average speed of said first ride; (d) said imputed information regarding said rider's profile; (e) said imputed information regarding said bicycle's profile; (f) said heartbeat data transmitted to said base unit and (g) said calories burned by said rider during said first ride; and, wherein said smartphone display screen displays to said rider during said first ride; said imputed information regarding said profile of said rider; said information regarding said profile of said bicycle; data provided by said GPS device; and at least one of: (1) said speeds of said bicycle during said first ride; (2) said distance traveled by said bicycle during said first ride; (3) said average speed of said first ride; and, (4) said calories burned by said rider during said first ride;

further comprising: a thermal sensor; an altitude sensor; wherein at least one of said smartphone microprocessor and said base unit microprocessor: (1) can determine atmospheric temperatures during said first ride; (2) can determine altitudes of said bicycle during said first ride; and, (3) can determine calories burned by said rider during said first ride based on said atmospheric temperatures and said altitudes; wherein said computer memory can store: (1) said atmospheric temperatures; and, (2) said altitudes; and, wherein said smartphone display screen displays to said rider during said first ride: (1) said atmospheric temperatures; and, (2) said altitudes;

wherein said smartphone display screen displays to said rider during said first ride: said speeds of said bicycle during said first ride; said distance traveled by said bicycle during said first ride; said average speed of said first ride; and, said calories burned by said rider during said first ride;

wherein: said conductive surface determines heartbeat data of said rider when said hand of said rider contacts said conductive surtax while said rider manually propels said bicycle during a second ride; at least one of said smartphone microprocessor and said base unit microprocessor: (1) can determine a distance traveled by said bicycle during said second ride based on data from said GPS device; (2) can determine an average speed of said second ride; (3) can determine calories burned by said rider during said second ride based on said heartbeat data, said rider's profile, said bicycle's profile, said distance traveled during said second ride, and said average speed of said second ride; (4) can determine atmospheric temperatures during said second ride; (5) can determine altitudes of said bicycle during said second ride; and, (6) computer memory can store: (a) said speeds of said bicycle during said second ride; (b) said distance traveled during said second ride; (c) said average speed of said second ride; (d) said atmospheric temperatures during said second ride; (e) said altitudes during said second ride; and, (d) said calories burned by said rider during said second ride; and, wherein said smartphone display screen displays to said rider during said second ride: (1) said imputed information regarding said profile of said rider; (2) said information regarding said profile of said bicycle; (3) data provided by said GPS device during said second ride; (4) said speeds of said bicycle during said second ride; (5) said distance traveled by said bicycle during said second ride; (6) said average speed of said second ride; (7) said atmospheric temperatures during said second ride; (8) said altitudes during said second ride; and, (9) said calories burned by said rider during said second ride; and wherein: said conductive surface is part an elastic grip that is attachable to said handle bar of said bicycle and to said second bicycle; and, a battery powered transmitter is positioned within said elastic grip and transmits said heartbeat data to at least one of said smartphone and said base unit.

2. The activity monitoring and recording device of claim 1 wherein said smartphone and said base unit comprises between them: (1) Bluetooth communication port; and, (2) a Universal Serial Bus (USB) interface.

3. The activity monitoring and recording device of claim 1 wherein said smartphone and said base and can communicate via at least one of: a modem and Wi-Fi.

4. The activity monitoring and recording device of claim 1 wherein said smartphone can transfer data related to at least one of said first ride and said second ride to at least one of: a tablet computer, a lap top computer, another smartphone and, a desk top computer and, cloud; wherein said activity monitoring and recording device can record the riders various type of physiological data, such as heartbeat, body temperature, and blood pressure via Bluetooth from any third party device; and, wherein said activity monitoring and recording device can record the environmental and atmospheric data, such as wind speed and humidity via Bluetooth from any third party device.

5. The activity monitoring and recording device of claim 4 wherein said smartphone can transfer said data related to at least one of said first ride and said second ride via a wired connection and wirelessly.

* * * * *